(12) United States Patent
Lauriol-Garbey et al.

(10) Patent No.: US 9,079,841 B2
(45) Date of Patent: *Jul. 14, 2015

(54) PROCESS FOR PREPARING ACROLEIN FROM GLYCEROL OR GLYCERIN

(75) Inventors: Pascaline Lauriol-Garbey, Lyons (FR);
Virginie Belliere-Baca, Andresy (FR);
Stéphane Loridant, Meyzieu (FR);
Jean-Marc Millet, Lyons (FR)

(73) Assignees: ADISSEO FRANCE S.A.S. (FR);
CENTRE NATIONAL DE LA RECHERCHE SCIENTIFIQUE (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/704,845

(22) PCT Filed: Jun. 16, 2011

(86) PCT No.: PCT/FR2011/051375
§ 371 (c)(1),
(2), (4) Date: Feb. 22, 2013

(87) PCT Pub. No.: WO2011/157959
PCT Pub. Date: Dec. 22, 2011

(65) Prior Publication Data
US 2013/0197258 A1 Aug. 1, 2013

(30) Foreign Application Priority Data
Jun. 17, 2010 (FR) ...................... 10 54794

(51) Int. Cl.
| | | |
|---|---|---|
| *C07C 45/66* | (2006.01) |
| *C07C 319/18* | (2006.01) |
| *C07C 49/29* | (2006.01) |
| *C07C 45/29* | (2006.01) |
| *B01J 21/06* | (2006.01) |
| *B01J 21/08* | (2006.01) |
| *B01J 23/30* | (2006.01) |
| *C07C 45/52* | (2006.01) |
| *C07C 319/20* | (2006.01) |
| *B01J 23/10* | (2006.01) |
| *B01J 23/20* | (2006.01) |
| *B01J 23/34* | (2006.01) |

(52) U.S. Cl.
CPC .............. *C07C 45/29* (2013.01); *B01J 21/063* (2013.01); *B01J 21/066* (2013.01); *B01J 21/08* (2013.01); *B01J 23/30* (2013.01); *C07C 45/52* (2013.01); *C07C 319/18* (2013.01); *C07C 319/20* (2013.01); *B01J 23/10* (2013.01); *B01J 23/20* (2013.01); *B01J 23/34* (2013.01)

(58) Field of Classification Search
USPC ........... 558/345, 315; 502/242, 309; 568/486, 568/41
See application file for complete search history.

(56) References Cited

U.S. PATENT DOCUMENTS

| | | | |
|---|---|---|---|
| 7,790,934 B2 | 9/2010 | Redlingshofer et al. | |
| 7,846,861 B2 | 12/2010 | Redlingshofer et al. | |
| 8,076,509 B2 * | 12/2011 | Kasuga et al. ................ | 562/532 |
| 2008/0183013 A1 | 7/2008 | Dubois et al. | |
| 2008/0214384 A1 | 9/2008 | Redlingshofer et al. | |
| 2010/0010260 A1 | 1/2010 | Kasunga | |
| 2010/0247407 A1 | 9/2010 | Larcher | |
| 2010/0247411 A1 | 9/2010 | Larcher | |
| 2011/0112330 A1 * | 5/2011 | Magatani et al. ............. | 568/486 |
| 2011/0160491 A1 * | 6/2011 | Dubois et al. ................ | 568/486 |
| 2011/0288323 A1 * | 11/2011 | Belliere-Baca et al. ...... | 558/315 |
| 2012/0330049 A1 * | 12/2012 | Paul et al. ..................... | 558/315 |

FOREIGN PATENT DOCUMENTS

| | | |
|---|---|---|
| FR | 2907444 A1 | 4/2008 |
| FR | 2907445 A1 | 4/2008 |
| FR | 2920767 A1 | 3/2009 |
| FR | 2938535 A1 | 5/2010 |
| JP | 2008266165 | 7/2008 |
| WO | 2006087083 A2 | 8/2006 |
| WO | 2006087084 A2 | 8/2006 |
| WO | 2007058221 A1 | 5/2007 |
| WO | 2007132926 A1 | 11/2007 |
| WO | 2008006977 A1 | 1/2008 |
| WO | 2008066079 A1 | 6/2008 |
| WO | 2009127889 A1 | 10/2009 |

OTHER PUBLICATIONS

Katryniok et al Green Chem. (2010), 12, 1922-1925.*
Song-Hai Chai et al. Green Chem. (2008), 10, 1087-1093.*
International Search Report issued Dec. 10, 2011, re: PCT/FR2011/051375, pp. 6; citing: US 2008/214384 A1, FR 2 920 767 A1, F 2 907 445 A1 and FR 2 938 535 A1.
M. Pagliaro et al. Angew. Chem. Int. Ed.; 2007; vol. 46, abstract.
M. Pagliaro et al., "The Future of Glycerol", 2008; abstract, RSC Publishing, Cambridge.

(Continued)

Primary Examiner — Nyeemah A Grazier
(74) Attorney, Agent, or Firm — Cantor Colburn LLP

(57) ABSTRACT

The invention concerns a method for preparing acrolein from glycerol or glycerine, wherein dehydration of the glycerol or glycerine is achieved in the presence of a catalyst based on zirconium oxide and which active phase consists in at least a) a silicon oxide, a zirconium oxide and at least one metal M oxide, said metal being selected from tungsten, cerium, manganese, niobium, tantalum, vanadium and titanium, b) a titanium oxide, a zirconium oxide and at least one metal M oxide, said metal being selected from tungsten, cerium, manganese, niobium, tantalum, vanadium and silicon.

This method can be used for making 3-(methylthio)propionic aldehyde MMP, 2-hydroxy-4-methylthiobutyronitrile HMTBN, methionine and its analogs.

14 Claims, 1 Drawing Sheet

(56) References Cited

OTHER PUBLICATIONS

Chai et al. "Sustainable production of acrolein: Preparation and characterization of zirconia-supported 12-tungstophosphoric acid catalyst for gas-phase dehydration of glycerol", Applied Catalysis A: General, 2009, pp. 213-222, vol. 353, Else.

Chai et al. "Sustainable production of acrolein: Gas-phase dehydration of glycerol over Nb2O5 catalyst" Journal of Catalysis 2007, 250, 342-349, published Aug. 6, 2007.

Lauriol-Garbey et al. "Acid-base properties of niobium-zirconium mixed oxide catalysts for glycerol dehydration by calorimetric and catalytic investigation" Applied Catalysis B Environmental 2011, 106, 94-102, published May 17, 2011.

Lauriol-Garbey et al. "New efficient and long life catalyst for gas-phase glycerol dehydration to acrolein" Journal of Catalysis 281 (2011) 362-370, published Jun. 23, 2011.

JP2007268363 A; published Oct. 18, 2007; Abstract only; 1 page.

Atia, et al. "Dehydration of glycerol in gas phase using heteropolyacid catalysts as active compounds", Journal of Catalysis, Academic, Aug. 15, 2008, pp. 71-82, vol. 258, No. 1, Academic Press, Duluth, MN USA.

Gutierrez, et al. "Mo and NiMo catalysts supported on SBA-15 modified by grafted ZrO2 species: Synthesis, characterized and evaluation in 4,6-dimethyldibenzothiophene hydrodesulfurization", Journal of Catalysis, 2007, pp. 140-153, vol. 249, Elsevier Inc.

Kantcheva et.al., "Characterization of Zr6Nb2O17 synthesized by a peroxo route as a novel solid acid", Catalysis Communications (2008), 9(5), p. 874-879.

Kleitz, et al. "Cubic Ia3d large mesoporous silica: synthesis and replication to platinum nanowires, carbon nanorods and carbon nanotubes", The Royal Society of Chemistry, ChemComm, 2003, pp. 2136-2137, Cambridge UK.

Kostova, et al. "Hexagonal mesoporous silicas with and without Zr as supports for HDS catalysts", Catalysis Today, 2001, pp. 217-223, vol. 65.

Ning, et al. "Glycerol Dehydration to Acrolein over Activated Carbon-Supported Silicotungstic Acids", Chinese Journal of Catalysis, Mar. 2008, pp. 212-214, vol. 29, No. 3.

PCT/FR2009/052577;International Search Report ; Dated Sep. 1, 2010.

PCT/FR2010/052855_Written Opinion , International Application Filing Date: Dec. 21, 2010; Date of Mailing Jan. 8, 2012, 6 pages; translation.

Tsukuda et al. "Production of acrolein from glycerol over silica-supported heteropoly acids", Catalysis Communications 8, 2007, pp. 1349-1353.

Zhao et al. "Triblock Copolymer Syntheses of Mesoporous Silica with Periodic 50 to 300 Angstrom Pores", Science, 1998, pp. 548-552, vol. 279, downloaded from www.sciencemag.org; May 17, 2012, DOI: 10.1126/science.279.5350.548.

\* cited by examiner

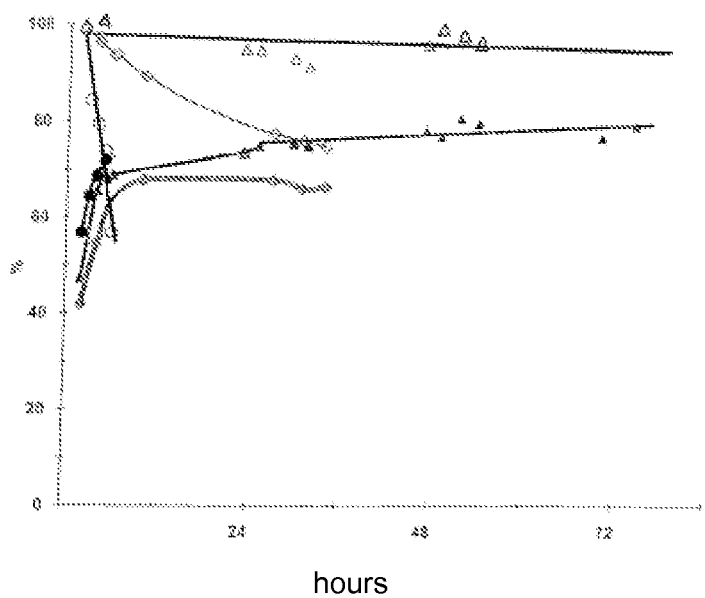
hours

PROCESS FOR PREPARING ACROLEIN FROM GLYCEROL OR GLYCERIN

TECHNICAL FIELD

The present invention relates to a catalytic method for making acrolein by dehydration of glycerol or glycerine and to the application of such a method.

BRIEF DISCUSSION OF RELATED ART

By glycerol is meant a glycerol either purified or not, preferably stemming from biomass and notably a highly purified or partly purified glycerol. A purified glycerol has a purity greater than or equal to 98%, obtained by distillation of glycerine. A non-purified or only partly purified glycerol may be in solution in methanol when it for example stems from transesterification of triglycerides, as described hereafter. By glycerine is notably meant glycerine of natural origin, stemming from hydrolysis of vegetable oils and/or animal fats, or more or less purified or refined or else raw glycerine of synthetic origin stemming from petroleum. As an example, raw glycerine has a titer comprised between 80 and 85%. Thus, subsequently in the description, reference is mainly made to the conversion of a glycerol or a glycerine stemming from biomass, but the invention of course is not limited thereto and its benefit extends to all glycerols and glycerines, regardless of their origins and their degrees of purity.

Gradual exhaustion of fossil energies leads industrials to envision the use of renewable raw materials stemming from the biomass for producing fuels. In this context, biodiesel is a fuel produced from vegetable or animal oil.

This product benefits from a green aura because of a clearly favorable $CO_2$ balance as compared with fossil energies. Diester® (or MEVOs, Methyl Esters of Vegetable Oils) is a biodiesel made by transesterification of triglycerides present in oleaginous liquids, notably palm, rapeseed and sunflower vegetable oils, by methanol. This transesterification co-produces approximately and according to the contemplated methods, 100 kg of glycerol per metric ton of Diester®. The non-lipid portion of the raw material used, the cakes, is mainly exploited in animal feed.

This biodiesel is used, mixed with diesel oil. European Directives 2001/77/EC and 2003/30/EC, which will be applied in the near future, plan to introduce 7% in 2010 and 10% by the year 2015 of Diester® in diesel oils. This substantial increase in the produced amount of biodiesel will generate significant amounts of glycerol equivalent to several hundreds of thousands of tons/year.

Some 1500 uses of glycerol have already been listed, among which the following illustrate its presence in many and various formulations, as examples:
  moisteners in pharmacy (in suppositories and syrups) or in cosmetology in moisturizing creams, glycerine soaps, toothpastes,
  solvents in the food industry,
  plasticizers or lubricants in the chemical industry.

These applications will prove to be clearly insufficient for absorbing the amounts of glycerol which will be co-produced with biodiesels and although in progress, the conventional glycerol market (soaps, pharmacy, . . . ) will not be able either to absorb such a surplus. It is therefore vital to find new applications with which the value of very large volumes of glycerol may be increased.

In view of this, many outlets have been investigated these recent years (see M. Pagliaro et al, *Angew. Chem. Int. Ed.* (2007) 46, 4434-4440 as well as M. Pagliaro, M Rossi: The Future of Glycerol, RSC Publishing, Cambridge (2008)), with in particular the six following routes for adding value thereto:
  conversion into 1,3-propanediol and into 1,2-propanediol, notably used as base monomers in the synthesis of polyesters and polyurethanes,
  conversion into monoesters for the chemistry of lubricants,
  conversion into polyglycerols used as emulsifiers, food additives,
  conversion into acrolein (by dehydration) and into acrylic acid (by dehydration and oxidation),
  direct addition of value as additives for animal feed.

Acrolein and acrylic acid are traditionally used by controlled oxidation in the gas phase of propylene by oxygen from air in the presence of catalysts based on molybdenum and/or bismuth oxides. The thereby obtained acrolein may either be directly integrated into a two-step method for producing acrylic acid, or be used as a synthesis intermediate. The production of both of these monomers is therefore closely related to propylene which in substance is produced by steam cracking or catalytic cracking of petroleum cuts.

The markets of acrolein, one of the simplest unsaturated aldehydes, and of acrylic acid are gigantic since these monomers enter the composition of many mass marketed products.

Moreover, acrolein, a highly reactive compound because of its structure, finds many applications, notably as a synthesis intermediate. It is most particularly used as a key intermediate entering the synthesis of D,L-methionine and of its hydroxyl-analog derivative, 2-hydroxy-4-methylthiobutanoic acid (HMTBA). These food additives are massively used since they enter the composition of food supplements indispensable to the growth of animals (poultry, pigs, ruminants, fish, . . . ). In a certain number of cases, it may be profitable to be able to increase, or even ensure production capacities of existing industrial units by diversifying the engaged raw material. It therefore appears to be most particularly of interest to be able to increase acrolein productivity, while reducing the dependency towards this resource stemming from petroleum which is propylene.

Methods for converting glycerol into acrolein via catalytic dehydration are known, according to the reaction:

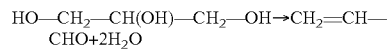

$$HO-CH_2-CH(OH)-CH_2-OH \rightarrow CH_2=CH-CHO + 2H_2O$$

Glycerol (also called glycerine) has been known for a long time as a source of acrolein (thermal transformation), it is a product which is widely found in nature, in the form of esters (triglycerides), in particular in all animal or vegetable oils and fats, which makes it a starting reagent available in sufficient quantity and in this respect may be used in industry. Actually, it is known that glycerol decomposes and gives acrolein when it is brought to temperatures above 280° C. This weakly selective reaction is accompanied by the formation of many by-products including acetaldehyde, hydroxyacetone, in addition to total oxidation products, CO, $CO_2$. It is therefore indispensable to control the reaction for transforming glycerol into acrolein in order to avoid unnecessary wasting of this resource and to do without a subsequent separation which is costly in energy with a complex acrolein purification process. Moreover, these impurities, mainly the aromatic derivatives are often at the origin of coke formation at the surface of the catalyst which poisons the latter over time; it is often necessary to regenerate the catalyst so as to again find satisfactory catalytic activity.

Many academic and industrial researchers have studied this reaction. The use of supercritical water as a reaction medium was notably contemplated. The use of a supercritical solvent on an industrial scale remains difficult for a continuous process because of particularly heavy infrastructures which require autoclaves operating under a very high pressure. On the other hand, the setting up of a continuous or batch process may be contemplated if a performing, selective and robust catalytic system is identified.

With view to the increasing interests for this chemical alternative, the literature mentions a great number of studies relating to the use of catalytic systems based on supported phosphor- or silico-tungstic heteropolyacids, mixed oxides and zeolites which may be used for continuous or batch processes in the liquid or gas phase.

Thus, documents WO-A-2006087083 and WO-A-2006087084 describe a method for catalytic dehydration of glycerol into acrolein in the gas phase, in the presence of molecular oxygen and of a strongly acid catalyst selected from zeolites, Nafion®, oxides of metals selected from aluminium, zirconium, titanium, niobium, tantalum, silicon, impregnated with acid functions in the form of sulfate, borate, tungstate, silicate and phosphate groups.

Document WO-A-2007132926 discloses a method for converting glycerol into acrolein in the presence of a catalyst selected from acid crystalline metallosilicates such as zeolites of the MFI or BEA structural type, comprising silicon and an element preferably selected from Al, Fe and Ga.

FR2920767A1 discloses a method for preparing acrolein or acrylic acid from glycerol, such as stemming from EMVOs. An aqueous solution of glycerol is vaporized in a fluidized bed and contacted with a solid catalyst for dehydration or oxydehydration reaction, in a fluidized bed. The used catalyst is chosen from any appropriate catalysts, notably zeolites; composites Nafion®, chlorinated aluminas; phosphotungstic and/or silicotungstic acids and acid salts and metal oxides impregnated with acid functional groups. A catalyst of W/ZrO$_2$—Si is specifically illustrated. This catalyst consists in tungstene oxide and zirconium oxide, which is then coated with silica.

US2008/214384A1 which relates to the same conversion, involves an acid tungsten-based catalyst, for example a catalyst consisting of montmorillonite, a tungsten oxide and a zirconium oxide. This document describes a process for regenerating this catalyst after it is used in the dehydration reaction of glycerol to acrolein where it has lost activity and/or selectivity. This regeneration is effected by exposing said catalyst alone, that is free of any entity involved in the dehydration, to an oxidizing or reducing atmosphere.

The quick loss of reactivity and/or selectivity is a disadvantage of these catalysts. Their regeneration process is generally long and cannot often be performed in situ. For illustration, the catalyst based on montmorillonite, a tungsten oxide and a zirconium oxide illustrated in US2008/214384A1 performs as follows:

at the end of 5 hours in the reaction mixture, the activity of the catalyst is strongly decreased;
the regeneration of the catalyst can't be performed in situ, it is actually done excluding any other entity;
the regeneration is long, about 5 hours.

BRIEF SUMMARY

The invention aims at overcoming the problems met with catalysts classically used for dehydrating glycerol into acrolein.

The invention is directed toward the application of robust, active, selective and regenerable catalysts, with which acrolein may be directly produced from glycerol or glycerine, notably stemming from the biomass.

With this alternative it is thus possible to have a competitive method for synthesizing acrolein, non-dependent on the propylene petroleum resource from another renewable raw material.

This possibility is particularly advantageous for synthesizing methionine or its analogs, such as its hydroxyl-analog (HMTBA) directly from the biomass.

Thus, the invention further relates to an application of this reaction to the synthesis of 3-(methylthio)propionic aldehyde (MMP), 2-hydroxy-4-methylthiobutyronitrile (HMTBN), methionine and its analogs such as 2-hydroxy-4-methylthiobutanoic acid (HMTBA), esters of HMTBA such as the isopropyl ester, 2-oxo-4-methylthiobutanoic acid, from acrolein.

Methionine, HMTBA and the esters of the latter and analogs are used in animal nutrition and in their industrial synthesis processes, acrolein is generally obtained by oxidation of propylene and/or of propane. Oxidation of propylene into acrolein by air in the presence of water is partial, and the resulting raw product, based on acrolein, also contains unreacted propylene and propane, water and by-products of the oxidation reaction, notably acids, aldehydes and alcohols.

As compared with known methods, according to the described invention, a method is provided for preparing acrolein from glycerol or glycerine, by catalytic dehydration of glycerol in the presence of a catalyst which, while allowing conversion of the totality of the initial glycerol, may both be very easy to regenerate and has a long lifetime. The authors of the invention discovered that this catalyst was based on zirconium oxide and which active phase comprises at least:

a) a silicon oxide, a zirconium oxide and at least one metal M oxide, said metal being selected from tungsten, cerium, manganese, niobium, tantalum, vanadium and titanium, b) a titanium oxide, a zirconium oxide and at least one metal M oxide, said metal being selected from tungsten, cerium, manganese, niobium, tantalum, titanium, vanadium and silicon.

Said oxides make up the active phase of the catalysts of the invention, in that they directly contribute to the catalytic properties of the catalyst. For example, a metallic oxide acting on the selectivity of the catalyst and/or on its texture (pore size, crystallite size, specific surface area) makes up the active phase; on the contrary, a metallic oxide only acting as a binder to bind the particles of the active phase, can't be considered as making up the active phase.

Thus, the invention relates to a method for obtaining acrolein from glycerol or glycerine, in the presence of a catalyst as defined above, and to the use of this catalyst for converting glycerol or glycerine into acrolein. A catalyst of the invention allows controlled conversion of glycerol or glycerine into acrolein, i.e. not promoting conversion as far as acrylic acid. For this purpose, a preferred catalyst of the invention does not comprise, or does not comprise in a majority weight proportion relatively to each of the other oxides making it up, of molybdenum oxide and/or copper oxide.

This is why the invention also relates to the use of at least any one of the catalysts a) and b) as defined earlier for converting glycerol or glycerine into acrolein.

The catalyst may be prepared in various ways (co-precipitation, hydrothermal synthesis . . . ). An effective procedure was described in patents FR 2907444 and FR 2907445.

The catalyst defined earlier may further meet the preferential characteristics below considered alone or as a combination:

the catalysts a) and b) only composed of the oxides defined earlier, at least one of the oxides of said catalysts a) and b) is supported, the molar ratio Zr/sum of the other constitutive elements of said catalysts a) and b) different from Zr, i.e. selected from Si, Ti, W and M, varies from 0.5 to 200, more advantageously it varies from 1 to 100.

As stated earlier, the catalyst of the invention has the benefit of being able to be easily regenerated, and this without affecting the yield of the dehydration or the acrolein selectivity.

The reaction according to the invention may be applied in a gas phase or in a liquid phase, preferably in a gas phase. When the reaction is conducted in a gas phase, different process technologies may be used, i.e. a fixed bed process, a fluidized bed process or a process with a circulating fluidized bed. In the first two processes, in a fixed bed or in a fluidized bed, the regeneration of the catalyst may be separated from the catalytic reaction. For example it may be accomplished ex situ with conventional regeneration methods, such as combustion in air or with a gas mixture containing molecular oxygen. According to the method of the invention, the regeneration may be accomplished in situ since the temperatures and pressures at which regeneration is accomplished are close to the reaction conditions of the process.

Regarding the liquid phase process, the reaction may be achieved in a conventional reactor for reaction in a liquid phase on a solid catalyst, but also in a reactor of the catalytic distillation type considering the significant difference between the boiling points of glycerol (290° C.) and of acrolein (53° C.). A process in a liquid phase may also reasonably be contemplated at a relatively low temperature which allows continuous distillation of the produced acrolein, thereby limiting the consecutive reactions of acrolein degradation. The experimental conditions of the reaction in the gas phase are preferably a temperature comprised between 250 and 400° C., at a pressure comprised between 1 and 10 bars. In the liquid phase, the reaction operates between 150 and 350° C. and at a pressure which may range from 3 to 70 bars.

Another advantage of the method of the invention lies in the form of the starting glycerol or glycerine which may be in pure or partly purified form or in solution, notably an aqueous solution. Advantageously, an aqueous solution of glycerol is used. In an aqueous solution, the concentration of the glycerol is preferably of at least 1%, at best it varies from 10 to 50% by weight and preferably between 15 and 30% by weight in the reactor. The glycerol concentration should not be too high for the purpose of avoiding parasitic reactions which burden the acrolein yield, like the formation of glycerol ethers or acetalization reactions between the produced acrolein and the non-converted glycerol. Moreover, the glycerol solution should not be too diluted, because of a redhibitory energy cost induced by the evaporation of the glycerol. In every case, it is easy to adjust the glycerol concentration of the solution by partly or totally recycling the water produced by the relevant reaction. Energy optimization at the bounds of the synthesis tends to recover heat at the reaction output in order to vaporize the flow of glycerol supplied to the reactor.

The invention further provides a method for making 3-(methylthio)propionic aldehyde (MMP), 2-hydroxy-4-methylthiobutyronitrile (HMTBN), methionine, 2-hydroxy-4-methylthiobutanoic acid (HMTBA), esters of the latter, notably the isopropyl ester, and 2-oxo-4-methylthiobutanoic acid (KMB) from acrolein, according to which the acrolein is obtained by a method described above. Comparatively to the conventional method for making acrolein by controlled oxidation of propylene, the acrolein produced according to the aforementioned method may contain impurities different from those of the traditional method, both under the angle of their amount and of their nature. According to the contemplated use, synthesis of acrylic acid or of methionine or its hydroxyl analog, purification of acrolein may be contemplated according to techniques known to one skilled in the art.

Thus, once the acrolein is directly obtained according to the invention or after purification, it is set to react with methylmercaptan (MSH) in order to produce 3-(methylthio)propionic aldehyde (or MMP). In a following step, the MMP is put into contact with hydrocyanic acid in order to produce 2-hydroxy-4-(methylthio) butyronitrile (HMTBN). After synthesis of HMTBN, various reaction steps lead to methionine, its hydroxyl analog (HMTBA), the esters of the latter or its oxo analogue (KMB). All these steps from the synthesis of acrolein are well known to one skilled in the art.

The present invention is now described in more detail and illustrated with the examples and figures hereafter without however limiting the scope thereof.

BRIEF DESCRIPTION OF THE DRAWING

The FIGURE shows the development of the conversion into glycerol and of the corresponding acrolein selectivity over time, on catalyst E described in the example 4; the catalyst E is a catalyst of the invention, the catalysts F and G are catalysts of the prior art.

DETAILED DESCRIPTION AND EXAMPLES

The time indicated for each point is that of the end of sampling corresponding to trapping for one hour. The reaction conditions and the calculation methods used by the acrolein conversion and selectivity are described later on.

This FIGURE is read, substantiated by the following caption:

conversion into glycerol on catalyst E (Δ), F(◇) or G(○)

acrolein selectivity on catalyst E(▲), F(◆) or G(●)

The reaction conditions and the methods for calculating the conversion and acrolein selectivity are described hereafter.

The reaction for dehydration of the glycerol is conducted on the indicated catalysts, at atmospheric pressure, in a straight reactor with a fixed bed of diameter 18 mm. The reactor is placed in an oven which allows the catalyst to be maintained at the reaction temperature which is 300° C. The volume of catalyst loaded into the reactor is 4.5 mL, which gives a bed height of about 1.8 cm. The reactor is fed with a flow rate of 3.77 g/h of aqueous solution with 20% by weight of glycerol. The aqueous solution is vaporized by means of a C.E.M (Controlled Evaporator Mixer) Bronkhorst® evaporator in the presence of a nitrogen flow rate of 75 mL/min. The glycerol/water/nitrogen molar relative portion is 2.3/46.3/51.4. The calculated contact time is of the order of 1.9 s i.e. a GHSV of 1930 h$^{-1}$. The contact time is defined as follows:

Contact time=catalyst volume×$P_{atm}$/(total molar flow rate×Temperature×R)

with $P_{atm}$=101,325 Pa, Temperature=25° C. and total molar flow rate=molar flow rate of glycerol+molar flow rate of water+molar flow rate of the inert gas.

After reaction, the products are condensed, two systems of condensations were used. Examples 7 to 10 were obtained with a system of three traps mounted in series. The first trap contains a known mass of water and is cooled by crushed ice. The two other traps contain ethanol and are cooled by a cryostat to −25° C. The trapping period is one hour and the feed rate is not interrupted during the changes of traps.

The formed products are analyzed by chromatography, two analyses are conducted for each sample:
- The main products of the reaction are analyzed by gas chromatography on a capillary column (Nukol, 30 m×0.53 mm) with a Shimadzu 2014 chromatograph provided with an FID detector. The quantified products during this analysis are: acrolein, acetaldehyde, acetone, propionaldehyde, hydroxypropanone, acetic acid, allyl alcohol and phenol;
- The remaining glycerol is quantified by gas chromatography with a Hewlett Packard chromatograph equipped with an FID detector and a capillary column (Carbowax or ZBwax, 30 m×0.32 mm).

The glycerol conversion, the acrolein selectivity and the yield of different products are defined as follows:

Glycerol conversion (%)=100×(1−number of remaining glycerol moles/number of introduced glycerol moles)

Acrolein selectivity (%)=100×(number of produced acrolein moles/number of reacted glycerol moles)

Yield of X (%)=K×100×number of produced X moles/number of introduced glycerol moles With K=1 if X is acrolein, acetone, hydroxypropanone, propanal or allyl alcohol; K=⅔ if X=acetaldehyde or acetic acid and K=2 if X=phenol.

EXAMPLE 1

Preparation and Characterization of the Catalyst a

A catalyst according to the invention of the tungstated zirconia type doped with silica is prepared. The preparation of this solid includes three steps. The first step is the synthesis of zirconium hydroxide hydrate by co-precipitation of a solution of zirconium oxonitrate $ZrO(NO_3)_2 \cdot xH_2O$ (Aldrich, 99%) and a 28% ammonia solution at pH=8.8. The second step consists of stabilizing the zirconium hydroxide hydrate with silicic species according to the procedure described by Nahas et. al (Journal of Catalysis 247 (2007), p 51-60). The zirconium hydroxide hydrate is placed in a glass flask containing an ammoniacal solution, the pH of which is adjusted to 11. The mixture is refluxed for 72 hrs and then filtered and washed with permuted water. The last step is the exchange between tungstic acid $H_2WO_4$ (Aldrich 99%) dissolved in hydrogen peroxide and zirconium hydroxide. The tungstic acid is dissolved in a 35% hydrogen peroxide solution at 60° C. The tungstic acid concentration of the solution is 0.04M. The tungstic acid solution is then cooled down to room temperature, and the zirconium hydroxide doped with silica is slowly added. The obtained solid is filtered and then calcined in air at 650° C. Its specific surface area is 40 m²/g. The niobium, silicon and zirconium contents of the solid were determined by ICP-OES. The W/Si/Zr molar composition of this catalyst is 4.7/1.4/93.9.

EXAMPLE 2

Preparation and Characterization of Catalysts B and C

Two catalysts according to the invention of the tungstated zirconia type doped with silica are prepared. The catalysts are prepared following the same protocol as the one for catalyst A, but, during the second step, the mixture is refluxed only for 24 hrs and then filtered and washed with permuted water. The tungstic acid concentration of the solution is 0.04M for catalyst B and 0.1M for catalyst C. Their specific surface areas are 92 and 82 m²/g respectively. The tungsten, silicon and zirconium contents of the solids were determined by ICP-OES. The $ZrO_2/SiO_2/WO_3$ molar compositions are 90.6/0.7/8.7 for B and 87.3/0.6/12.1 for C.

EXAMPLE 3

Preparation and Characterization of Catalyst D (not Part of the Invention)

Catalyst D is of the tungstated zirconia. It is prepared following the same protocol as the one for catalyst B but without the second step, that is without the addition of silica. The specific surface area is 92 m²/g. The tungsten and zirconium contents of the solids were determined by ICP-OES. The $ZrO_2/WO_3$ molar composition of this catalyst is 92.5/7.5.

EXAMPLE 4

Preparation and Characterization of the Catalyst E

The ZrTiSiW catalyst according to the invention was prepared by Rhodia according to the method described in patent FR2907445A. The specific surface area of this catalyst was determined by the method BET (Brunauer Emmet and Teller) at −196° C. using a Micromeritics ASAP 2020 device. The solids are first desorbed at 300° C. during 3 hours under vacuum at $5 \times 10^{-5}$ bar. It is 105 m²/g. The weight composition of oxides of this catalyst is 54% of $ZrO_2$, 35% of $TiO_2$, 7.5% of $SiO_2$ and 3.5% of $WO_3$.

EXAMPLE 5

Preparation and Characterization of the Catalyst F (a Comparative Catalyst from the Prior Art)

The catalyst F is a tungstated zirconia (89.5% $ZrO_2$-10.5% $WO_3$) synthesised by Daiichi Kigenso (supplier reference: Z-1104). The specific surface area of this catalyst is 77 m²/g.

EXAMPLE 6

Preparation and Characterization of the Catalyst G (a Comparative Catalyst from the Prior Art)

Catalyst G is an H-ZSM-5 zeolite provided by Zeochem (ZEOcat PZ-2/5OH). The specific surface area of this catalyst determined is 406 m²/g.

EXAMPLE 7

Catalytic Dehydration of Glycerol into Acrolein: Evaluation of the Catalysts E, F and G Table 1 gives the performances obtained with the catalysts E, F and G at 6 hrs of reaction.

TABLE 1

|  | E (invention) | F (comparative) | G (comparative) |
|---|---|---|---|
| Conversion of glycerol | 100 | 94 | 57 |
| Acrolein selectivity | 69 | 64 | 65 |
| Acrolein yield | 69 | 60 | 37 |
| Acetaldehyde yield | 6.5 | 3.9 | 0.6 |
| Propionaldehyde yield | 5.4 | 2.8 | 1.6 |
| Acetone yield | 2.7 | 1.6 | 0.0 |
| Allyl alcohol | 0.5 | 0.5 | 0.2 |

TABLE 1-continued

|  | E (invention) | F (comparative) | G (comparative) |
|---|---|---|---|
| Hydroxypropanone yield | 3.1 | 6.1 | 3.0 |
| Phenol yield | 0.8 | 0.3 | — |

This table shows that with an equal catalyst volume, only catalyst E (according to the invention) allows total conversion of the glycerol. Further, with the catalysts of the invention, it is possible to obtain better acrolein selectivity, already visible at 6 hrs and which is confirmed at 50 hrs, with an acrolein yield of 80% for catalyst E.

Catalyst E is therefore more active and more selective than the catalysts of the prior art.

EXAMPLE 8

Catalytic Dehydration of Glycerol into Acrolein:
Time-Dependent Change of the Performances of the Catalysts E, F and G The change in the performances of the catalyst E, F and G over time, obtained under the same conditions as in Example 7 is shown in FIGURE.

Catalyst E of the invention maintains constant acrolein selectivity and high glycerol conversion over several days unlike the catalysts F and G of the prior art which are strongly deactivated within less than 24 hrs.

Catalyst E of the invention is therefore more active, more acrolein-selective but also more stable over time than the best catalysts claimed in the prior art.

EXAMPLE 9

Catalytic Dehydration of Glycerol into Acrolein:
Evaluation of the Catalyst A (According to the Invention)

Table 2 gives the performances of the catalyst A

TABLE 2

|  | Hour at the end of the sampling | | |
|---|---|---|---|
|  | 4 | 23 | 42 |
| Glycerol conversion | 98 | 96 | 87 |
| Acrolein selectivity | 68 | 80 | 83 |
| Acrolein yield | 67 | 77 | 72 |
| Actetaldehyde yield | 4.2 | 3.5 | 2.4 |

TABLE 2-continued

|  | Hour at the end of the sampling | | |
|---|---|---|---|
|  | 4 | 23 | 42 |
| Propionaldehyde yield | 3.1 | 2.4 | 1.6 |
| Acetone yield | 1.2 | 1.3 | 0.9 |
| Allyl alcohol yield | 0.7 | 0.9 | 0.6 |
| Hydroxypropanone yield | 5.2 | 10.9 | 9.7 |
| Phenol yield | 0.8 | 0.2 | — |

EXAMPLE 10

Catalytic Dehydration of Glycerol into Acrolein:
Evaluation of the Catalysts C and D (According to the Invention) and D (Out of Invention)

Table 3 gives the performances of the catalysts B, C and D. The effects of silicon added in low amount as a dope is clearly evident from the comparison with catalysts B and D. The comparison with catalysts B and C shows that performances that are as high as those obtained with tungsten or highest are obtained.

TABLE 3

|  | catalyseur D | | catalyseur B | | | | catalyseur C | | | |
|---|---|---|---|---|---|---|---|---|---|---|
|  | Hour at the end of the sampling | | | | | | | | | |
|  | 8 | 29 | 8 | 30 | 75 | 97 | 6 | 29 | 71 | 145 |
| Glycérol conversion | 100 | 71 | 100 | 100 | 96 | 94 | 100 | 99 | 95 | 77 |
| Acrolein yield | 61 | 50.2 | 63.2 | 75.6 | 75.3 | 72.6 | 65.3 | 74.3 | 77.7 | 56.9 |
| Acetaldehyde yield | 4.9 | 2.5 | 7.4 | 6.8 | 5.1 | 4.3 | 7.3 | 6.0 | 4.0 | 1.9 |
| Propionaldehyde yield | 5.7 | 4.0 | 5.3 | 4.7 | 3.7 | 3.4 | 4.6 | 3.7 | 3.0 | 1.4 |
| Acetone yield | 1.9 | 0.7 | 2.5 | 2.6 | 2.3 | 2.0 | 2.7 | 3.0 | 2.2 | 1.0 |
| Allyl alcool yield | 0.4 | 0.9 | — | 0.5 | 0.8 | 1.1 | 0.6 | 0.2 | 0.5 | 0.8 |
| Hydroxypropanone yield | 3.6 | 8.6 | 0.9 | 4.9 | 7.9 | 9.0 | 4.5 | 4.1 | 8.2 | 9.1 |
| Phenol yield (%) | 1.1 | 0.1 | 1.8 | 0.8 | 0.3 | 0.2 | 1.7 | 0.4 | 0.1 | — |

Catalyst mass, used in standard conditions: 6.96 g.

The invention claimed is:

1. A method for preparing acrolein from glycerol or glycerine, wherein dehydration of the glycerol or glycerine is achieved in the presence of a catalyst based on zirconium oxide, active phase of the catalyst resulting from calcination comprising at least
   a) a silicon oxide, a zirconium oxide and at least one metal M oxide, said metal being selected from the group consisting of tungsten, cerium, manganese, niobium, tantalum, vanadium and titanium, or
   b) a titanium oxide, a zirconium oxide and at least one metal M oxide, said metal being selected from the group consisting of tungsten, cerium, manganese, niobium, tantalum, vanadium and silicon.

2. The method according to claim 1, wherein the active phase comprises at least a silicon oxide, a zirconium oxide, a tungsten oxide and at least one metal M oxide, said metal being selected from the group consisting of cerium, manganese, niobium, tantalum, vanadium and titanium.

3. The method according to claim 2, wherein the metal is titanium.

4. The method according to claim 1, wherein at least one of the oxides of said catalyst a) and b) is supported.

5. The method according to claim 1, wherein the (Zr/sum of the elements Si, Ti, W and M, different from Zr) molar ratio varies from 0.5 to 200.

6. The method according to claim 5, wherein said molar ratio varies from 1 to 100.

7. The method according to claim 1, wherein the glycerol is in aqueous solution at a concentration of at least 1% by weight.

8. The method according to claim 7, wherein the glycerol concentration of the aqueous solution varies from 10 to 50% by weight.

9. The method according to claim 1, wherein the catalyst is regenerated.

10. A method for making 3-(methylthio)propionic aldehyde (MMP), 2-hydroxy-4-methylthiobutyronitrile (HMTBN), methionine, 2-hydroxy-4-methylthiobutanoic acid (HMTBA), esters of the latter, or 2-oxo-methylthiobutanoic acid (KMB), from acrolein, comprising providing the acrolein obtained with a method according to claim 1; and reacting the acrolein with methylmercaptan (MSH) to produce 3-(methylthio)propionic aldehyde (MMP); and/or contacting the 3-(methylthio)propionic aldehyde (MMP) with hydrocyanic acid to produce 2-hydroxy-4-(methylthio)butryronitrile (HMTBN); and/or producing methionine, 2-hydroxy-4-methylthiobutanoic acid (HMTBA), esters of the latter, or 2-oxo-methylthiobutanoic acid (KMB) from 2-hydroxy-4-(methylthio)butryronitrile (HMTBN).

11. The method according to claim 1, wherein the hydration reaction is conducted in a gas phase.

12. The method according to claim 11, wherein the dehydration reaction is conducted in a reactor with a fixed bed, a fluidized bed or a circulating fluidized bed.

13. The method according to claim 1, wherein the dehydration reaction is conducted in a liquid phase.

14. The method according to claim 1, wherein the active phase of the catalyst comprises a silicon oxide, a zirconium oxide, and at least one metal M oxide, said metal being selected from the group consisting of tungsten, cerium, manganese, niobium, tantalum, vanadium and titanium.

* * * * *